United States Patent
Farkas et al.

(10) Patent No.: US 10,571,381 B2
(45) Date of Patent: Feb. 25, 2020

(54) VIBRATING MEMBER FOR A VIBRATING DENSITOMETER

(71) Applicant: Micro Motion, Inc., Boulder, CO (US)

(72) Inventors: Felix Attila Farkas, Hunedoara (RO); Megan Casey, Boulder, CO (US); Roman Alexandru-Vlad, Cluj-Napoca (RO)

(73) Assignee: Micron Motion, Inc., Boulder, CO (US)

( * ) Notice: Subject to any disclaimer, the term of this patent is extended or adjusted under 35 U.S.C. 154(b) by 206 days.

(21) Appl. No.: 15/559,369

(22) PCT Filed: Mar. 30, 2015

(86) PCT No.: PCT/IB2015/000581
§ 371 (c)(1),
(2) Date: Sep. 18, 2017

(87) PCT Pub. No.: WO2016/156903
PCT Pub. Date: Oct. 6, 2016

(65) Prior Publication Data
US 2018/0073968 A1    Mar. 15, 2018

(51) Int. Cl.
*G01N 9/00* (2006.01)
(52) U.S. Cl.
CPC ....... *G01N 9/002* (2013.01); *G01N 2009/006* (2013.01); *G01N 2291/02818* (2013.01)
(58) Field of Classification Search
CPC ............................................. G01N 2291/2818
USPC ............................................................. 73/32
See application file for complete search history.

(56) References Cited

U.S. PATENT DOCUMENTS

| | | | |
|---|---|---|---|
| 3,848,466 A | 11/1974 | Dial et al. | |
| 5,373,745 A * | 12/1994 | Cage | G01F 1/8409 73/861.18 |
| 6,647,807 B2 | 11/2003 | Drahm et al. | |
| 2012/0072128 A1* | 3/2012 | Gao | G01N 35/00 702/23 |
| 2012/0160035 A1* | 6/2012 | Casey | C23C 10/06 73/861.355 |
| 2013/0133418 A1* | 5/2013 | Van Cleve | G01N 9/002 73/32 A |

FOREIGN PATENT DOCUMENTS

| | | |
|---|---|---|
| WO | 2014051574 A1 | 4/2014 |
| WO | 2014163642 A1 | 10/2014 |

* cited by examiner

*Primary Examiner* — Natalie Huls
*Assistant Examiner* — Monica S Young
(74) *Attorney, Agent, or Firm* — The Ollila Law Group LLC

(57) ABSTRACT

A vibrating member adapted for use in a vibrating densitometer is provided. The vibrating member comprises a base and a vibrating tube portion affixed to the base. The vibrating tube portion comprises an inner diameter and an outer diameter, wherein the inner diameter is axially shifted from the outer diameter such that the inner diameter is not concentric with the outer diameter, and wherein the axial shift increases a frequency separation between vibration modes in the vibrating tube portion.

26 Claims, 8 Drawing Sheets

VIBRATING MEMBER FOR A VIBRATING DENSITOMETER

FIELD OF THE INVENTION

The present invention relates to a vibrating densitometer, and more particularly, to a vibrating member of a vibrating densitometer.

BACKGROUND OF THE INVENTION

Densitometers are generally known in the art and are used to measure a density of a fluid. The fluid may comprise a liquid, a gas, a liquid with suspended particulates and/or entrained gas, or combinations thereof.

Vibrating densitometers can comprise a vibrating member, such as a cylinder that is exposed to a fluid under test. One example of a vibrating densitometer comprises a cylindrical conduit that is cantilever-mounted, with an inlet end coupled to an existing pipeline or other structure and with the outlet end free to vibrate. The conduit can be vibrated and a resonant frequency can be measured. As is generally known in the art, the density of the fluid under test can be determined by measuring a resonant frequency of the conduit in the presence of a fluid. According to well-known principles, the resonant frequency of the conduit will vary inversely with the density of the fluid that is contacting the conduit.

FIG. 1 shows a prior art vibrating cylinder of a vibrating gas densitometer. The prior art round vibrating cylinder may be vibrated at or near to a natural (i.e., resonant) frequency. By measuring a resonant frequency of the cylinder in a presence of a gas, the density of the gas can be determined. The prior art vibrating cylinder may be formed of metal and is constructed of a uniform thickness so that variations and/or imperfections in the cylinder wall do not affect the resonant frequency of the vibrating cylinder.

In theory, a cylinder having a perfectly round and uniform cross-sectional shape will result in only one three-lobed frequency mode shape, as is illustrated by FIG. 2. However, turning to FIG. 3, real world asymmetries caused by tolerance differences and other irregularities or imperfections will result in a supposedly circular tube, producing two vibration mode shapes that are very close together in frequency. This is problematic, as it may be practically impossible to distinguish between the two vibration modes. As a result, prior art vibrating densitometers may generate a resonant frequency value that is a mixture or combination of the two vibration modes, introducing errors into the density measurement.

FIG. 4 illustrates a prior art densitometer. The prior art densitometer includes a cylindrical vibrating member located at least partially within a housing. The housing or the vibrating member may include flanges or other members for operatively coupling the densitometer to a pipeline or similar fluid delivering device in a fluid-tight manner. In the example shown, the vibrating member is cantilever-mounted to the housing at an inlet end, leaving the opposite end free to vibrate. The vibrating member includes a plurality of fluid apertures that allow fluid to enter the densitometer and flow between the housing and the vibrating member. Therefore, the fluid contacts the inside as well as the outside surfaces of the vibrating member. This is particularly helpful when the fluid under test comprises a gas, as a greater surface area is exposed to the gas. In other examples, apertures may be provided in the housing and the vibrating member apertures may not be required.

A driver and a vibration sensor are positioned within the cylinder. The driver receives a drive signal from a meter electronics and vibrates the vibrating member at or near a resonant frequency. The vibration sensor detects the vibration of the vibrating member and sends the vibration information to the meter electronics for processing. The meter electronics determines the resonant frequency of the vibrating member and generates a density measurement from the measured resonant frequency.

To obtain accurate density measurements, the resonant frequency must be very stable. One prior art approach to achieve the desired stability is to vibrate the vibrating member in a radial vibration mode. In a radial vibration mode, the longitudinal axis of the vibrating member remains essentially stationary while at least a part of the vibrating member's wall translates and/or rotates away from its rest position. Radial vibration modes are preferred in straight conduit densitometers because radial vibration modes are self-balancing and thus, the mounting characteristics of the vibrating member are not as critical compared to some other vibration modes. FIG. 3 shows the motion of a wall of a vibrating member, exhibiting a first radial vibration mode and a second radial vibration mode. This is an example of a radial vibration mode that comprises a three-lobed radial vibration shape.

A key design criterion for a gas density cylinder is the separation the vibration mode shapes so that the mode shapes can be easily and accurately discriminated. If the vibrating member has a perfectly round cross-sectional shape and has a perfectly uniform wall thickness, there is only one three-lobed radial vibration mode. However, due to design tolerances, this is usually not achievable. Consequently, when a manufacturer attempts to make a perfectly round vibrating member with a perfectly uniform wall thickness, small imperfections result in two three-lobed radial vibrations that vibrate at two vibration modes that are very close to one another in frequency. The frequency separation between the two modes is typically very small and may be less than one Hertz, for example. With the two frequencies close together, a density determination may be difficult or impossible.

In some prior art densitometers, this problem is addressed by tuning the vibrating member so that it possesses a minimum frequency separation between the radial vibration modes. The tuning can be accomplished according to a variety of techniques, including forming lengthwise thicker and thinner regions in the vibrating member's wall in axially aligned strips. However, this prior art thickness tuning still requires extremely tight tolerances and results in manufacturing difficulties and high costs.

Therefore, there exists a need for a vibrating densitometer with increased vibration mode separation.

SUMMARY

A vibrating member adapted for use in a vibrating densitometer is provided according to an embodiment. The embodiment comprises a base and a vibrating tube portion affixed to the base. The vibrating tube portion comprises an inner diameter and an outer diameter, wherein the inner diameter is axially shifted from the outer diameter such that the inner diameter is not concentric with the outer diameter, and wherein the axial shift increases a frequency separation between vibration modes in the vibrating tube portion.

A method of forming a vibrating member adapted for use in a vibrating densitometer is provided. The method comprises the steps of forming a base; forming a vibrating tube portion comprising an inner diameter and an outer diameter, wherein the inner diameter is axially shifted from the outer diameter such that the inner diameter is not concentric with the outer diameter, and wherein the axial shift increases a frequency separation between vibration modes in the vibrating tube portion; and affixing the vibrating tube portion to the base.

Aspects

In one aspect, a vibrating member is adapted for use in a vibrating densitometer, comprising a base and a vibrating tube portion affixed to the base. The vibrating tube portion comprises an inner diameter and an outer diameter, wherein the inner diameter is axially shifted from the outer diameter such that the inner diameter is not concentric with the outer diameter, and wherein the axial shift increases a frequency separation between vibration modes in the vibrating tube portion.

Preferably, the vibrating tube portion is configured to be vibrated in one or more radial vibration modes.

Preferably, the vibrating tube portion comprises a first cross-sectional portion having a first thickness, and a second cross-sectional portion having a second thickness, wherein the first thickness is smaller than the second thickness.

Preferably, the first thickness is diametrically opposed to the second thickness.

Preferably, a wall thickness of the vibrating tube portion between the first thickness and the second thickness comprises a gradient of wall thickness that increases from the first thickness to the second thickness along a circumference of the vibrating tube portion.

Preferably, the first thickness is between about 0.02 mm and about 0.30 mm, and the second thickness is between about 0.02 mm and about 0.30 mm.

Preferably, the first thickness is between about 0.04 mm and about 0.09 mm, and the second thickness is between about 0.14 mm and about 0.18 mm.

Preferably, the vibrating tube portion comprises an average wall thickness between about 0.08 mm and 0.25 mm.

Preferably, the axial shift is between about 0.02 mm and 0.06 mm.

Preferably, the frequency separation between vibration modes in the vibrating tube portion is between about 2 Hz and 200 Hz.

Preferably, the frequency separation between vibration modes in the vibrating tube portion is between about 5 Hz and 50 Hz.

Preferably, the vibrating tube portion is included in a housing of a vibrating densitometer.

Preferably, the vibrating densitometer comprises a driver configured to vibrate the vibrating tube portion with respect to the housing, and at least one vibration sensor configured to detect vibrations of the vibrating tube portion.

In one aspect, a method of forming a vibrating member adapted for use in a vibrating densitometer is provided. The method comprises forming a base and forming a vibrating tube portion comprising an inner diameter and an outer diameter, wherein the inner diameter is axially shifted from the outer diameter such that the inner diameter is not concentric with the outer diameter, and wherein the axial shift increases a frequency separation between vibration modes in the vibrating tube portion. The method also comprises affixing the vibrating tube portion to the base.

Preferably, the method comprises the step of configuring the vibrating tube portion to be vibrated in one or more radial vibration modes.

Preferably, the step of forming a vibrating tube portion comprises: forming a first cross-sectional portion having a first thickness; and forming a second cross-sectional portion having a second thickness, wherein the first thickness is smaller than the second thickness.

Preferably, the step of forming a vibrating tube portion comprises forming the first thickness to be diametrically opposed to the second thickness.

Preferably, the step of forming a vibrating tube portion comprises forming a wall thickness of the vibrating tube portion between the first thickness and the second thickness to be variable, thus forming a gradient of wall thickness that increases from the first thickness to the second thickness along a circumference of the vibrating tube portion.

Preferably, the step of forming a first cross-sectional portion comprises forming the first thickness to be between about 0.02 mm and about 0.30 mm, and forming the second thickness to be between about 0.02 mm and about 0.30 mm.

Preferably, the step of forming a first cross-sectional portion comprises forming the first thickness to be between about 0.04 mm and about 0.09 mm, and forming the second thickness to be between about 0.14 mm and about 0.18 mm.

Preferably, the step of forming a vibrating tube portion comprises forming an average wall thickness of the vibrating tube portion to be between about 0.08 mm and 0.25 mm.

Preferably, the axial shift is between about 0.02 mm and 0.06 mm.

Preferably, the frequency separation between vibration modes in the vibrating tube portion is between about 2 Hz and 200 Hz.

Preferably, the frequency separation between vibration modes in the vibrating tube portion is between about 5 Hz and 50 Hz.

Preferably, the frequency separation between vibration modes in the vibrating tube portion is between about 2 Hz and 200 Hz.

Preferably, the step of providing a housing of a vibrating densitometer configured to house the vibrating tube portion.

Preferably, the method comprises the steps of: providing a driver configured to vibrate the vibrating tube portion with respect to the housing; and providing at least one vibration sensor configured to detect vibrations of the vibrating tube portion.

DESCRIPTION OF THE DRAWINGS

The same reference number represents the same element on all drawings. The drawings are not necessarily to scale.

DETAILED DESCRIPTION OF THE INVENTION

FIGS. 5-9 and the following description depict specific examples to teach those skilled in the art how to make and use the best mode of the invention. For the purpose of teaching inventive principles, some conventional aspects have been simplified or omitted. Those skilled in the art will appreciate variations from these examples that fall within the scope of the invention and will appreciate that the features described below can be combined in various ways to form multiple variations of the invention. As a result, the invention is not limited to the specific examples described below, but only by the claims and their equivalents.

Figure 5:
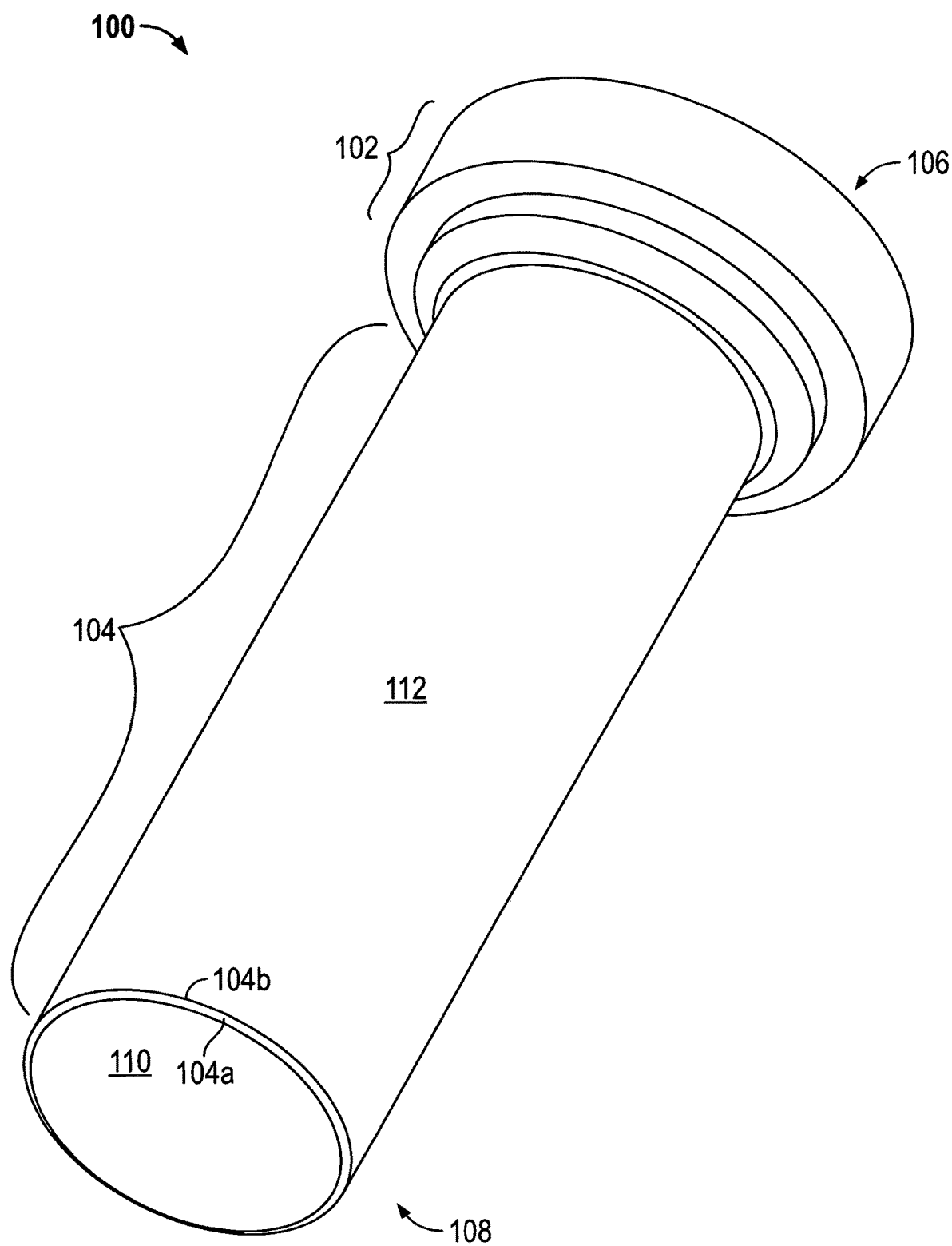
FIG. 5 shows a vibrating member for use in a vibrating densitometer according to an embodiment.
Figure 6:
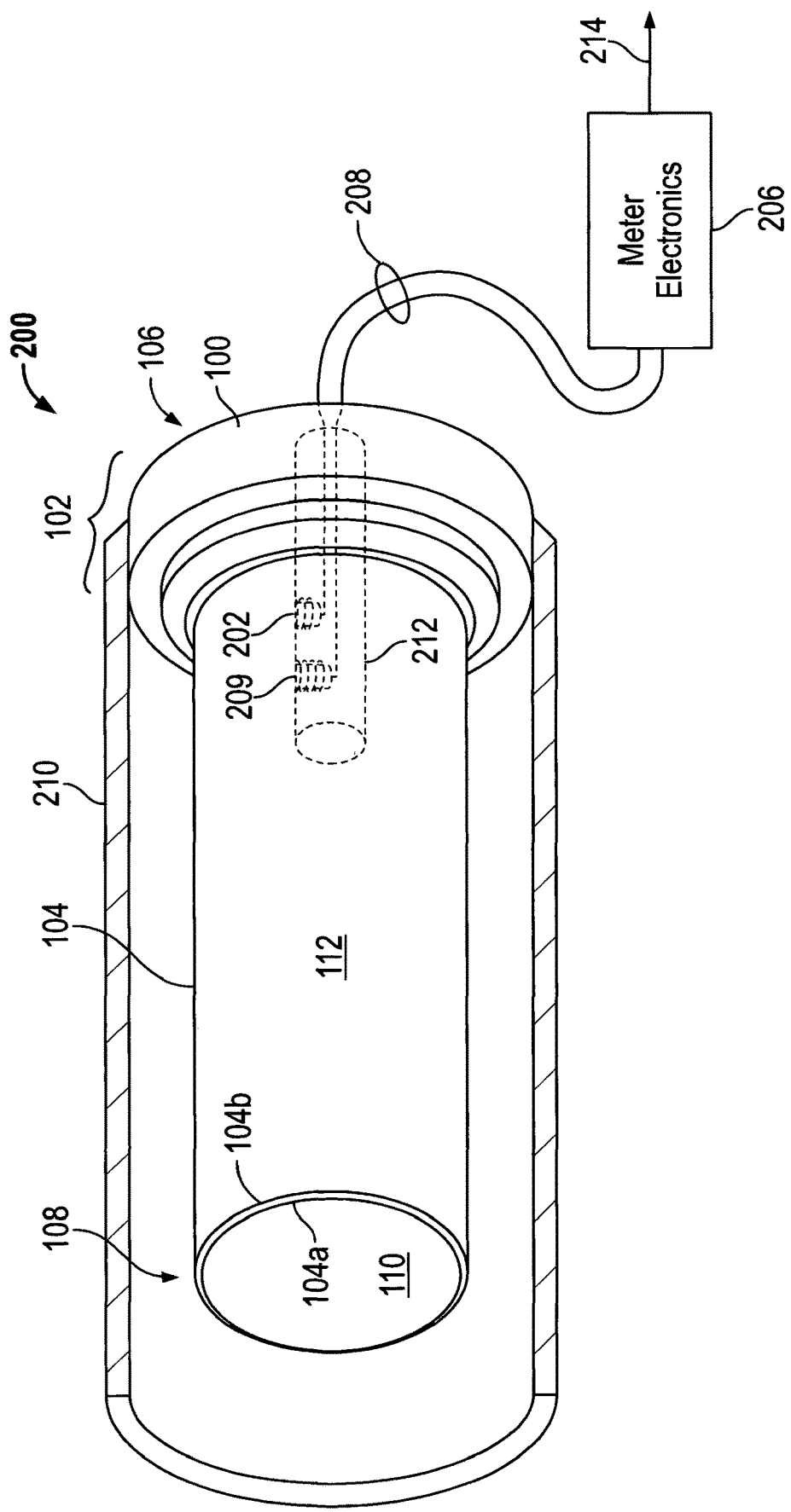
FIG. 6 shows a vibrating densitometer according to an embodiment.

FIG. 5 shows a vibrating member 100 for use in a vibrating densitometer 200 (see FIGS. 6 and 8) according to an embodiment of the invention. The vibrating member 100 in the embodiment shown includes a base 102 and an elongated vibrating tube portion 104 affixed to the base 102. The vibrating member 100 is substantially hollow and includes an inlet end 106 and an outlet end 108. The base 102 is located at the inlet end 106 of the vibrating member 100. The inlet end 106 may be coupled to a housing 210 (see FIGS. 6 and 8) or other component of the vibrating densitometer 200. Fluid entering or passing through the vibrating member 100 enters at the inlet end 106 and may exit at the outlet end 108. It will be appreciated that in an embodiment the inlet end 106 may be configured to be an outlet while the outlet end 108 may be configured to be an inlet.

Figure 1:
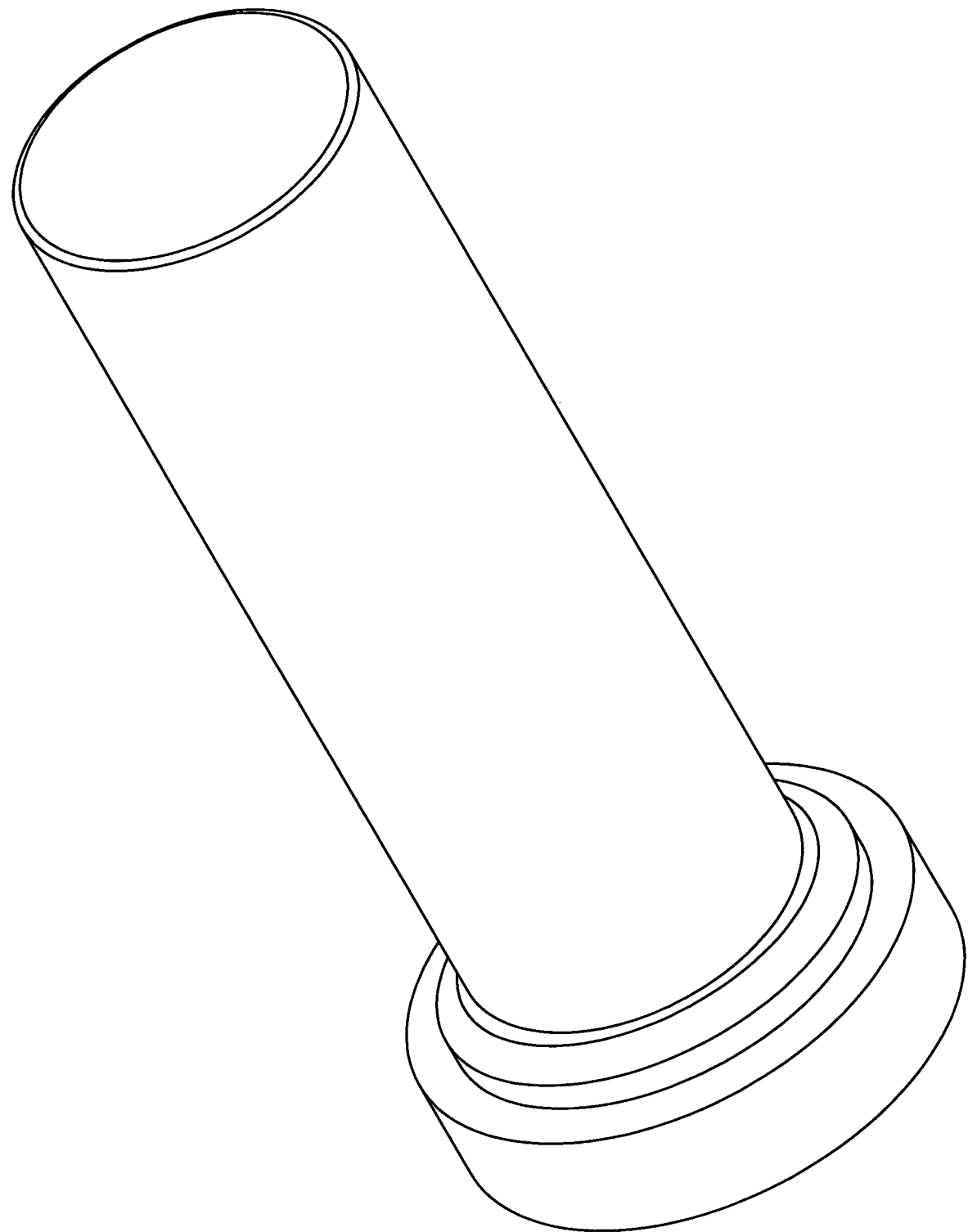
FIG. 1 shows a prior art vibrating cylinder of a vibrating gas densitometer.
Figure 2:
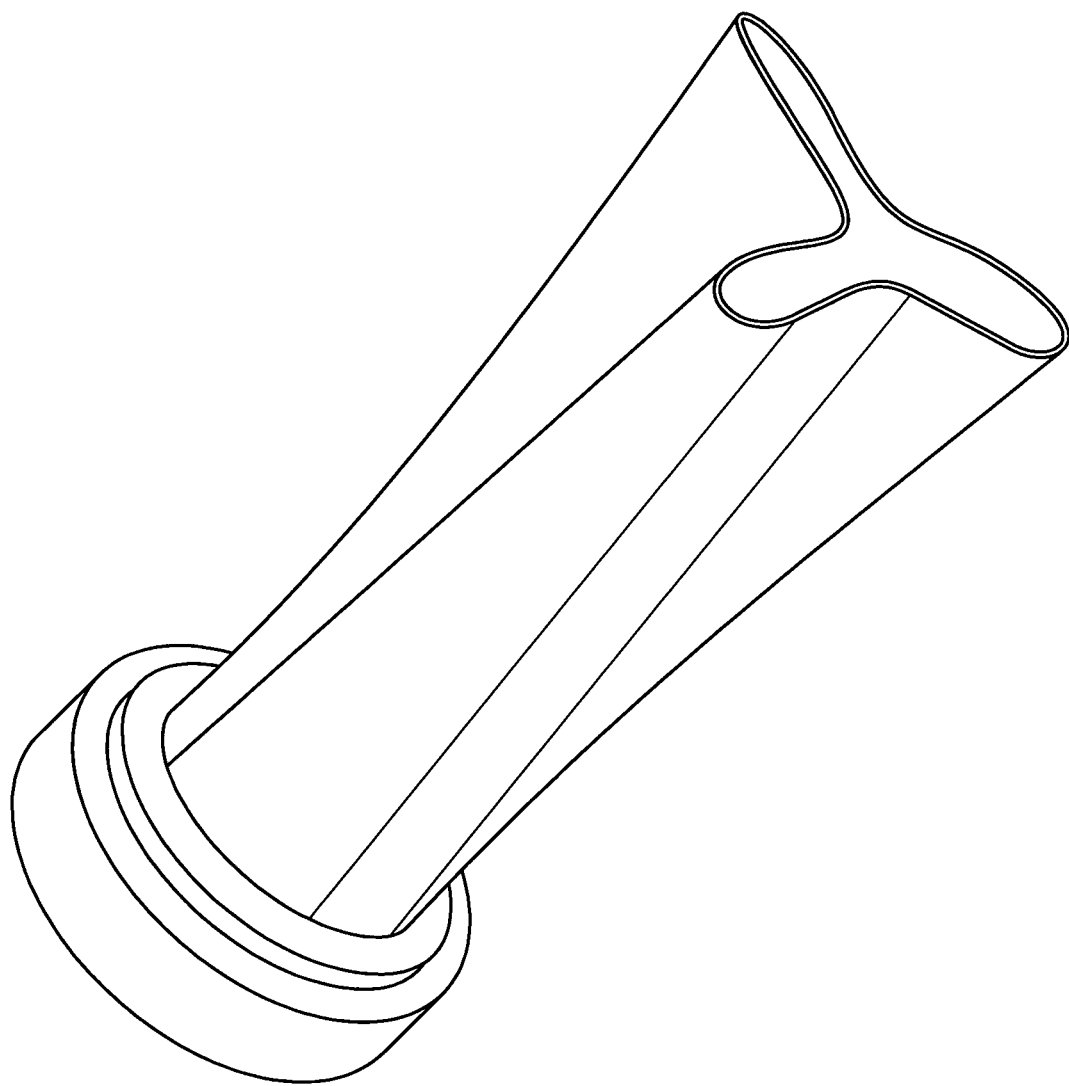
FIG. 2 shows the prior art vibrating cylinder of FIG. 1 vibrating in a radial mode.
Figure 3:
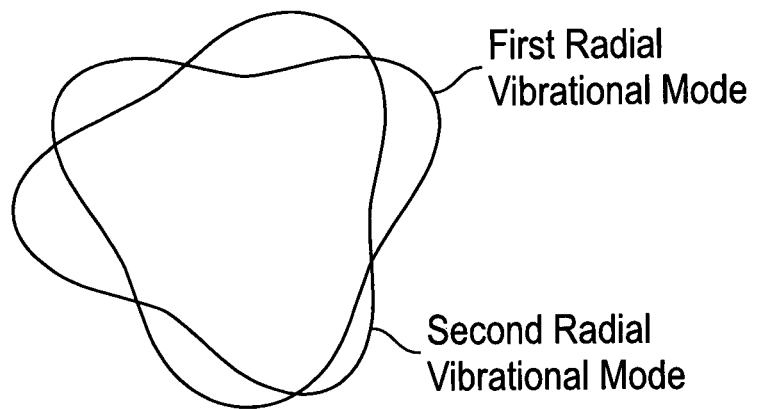
FIG. 3 shows the motion of a wall of a vibrating member exhibiting a first radial vibration mode and a second radial vibration mode.
Figure 4:
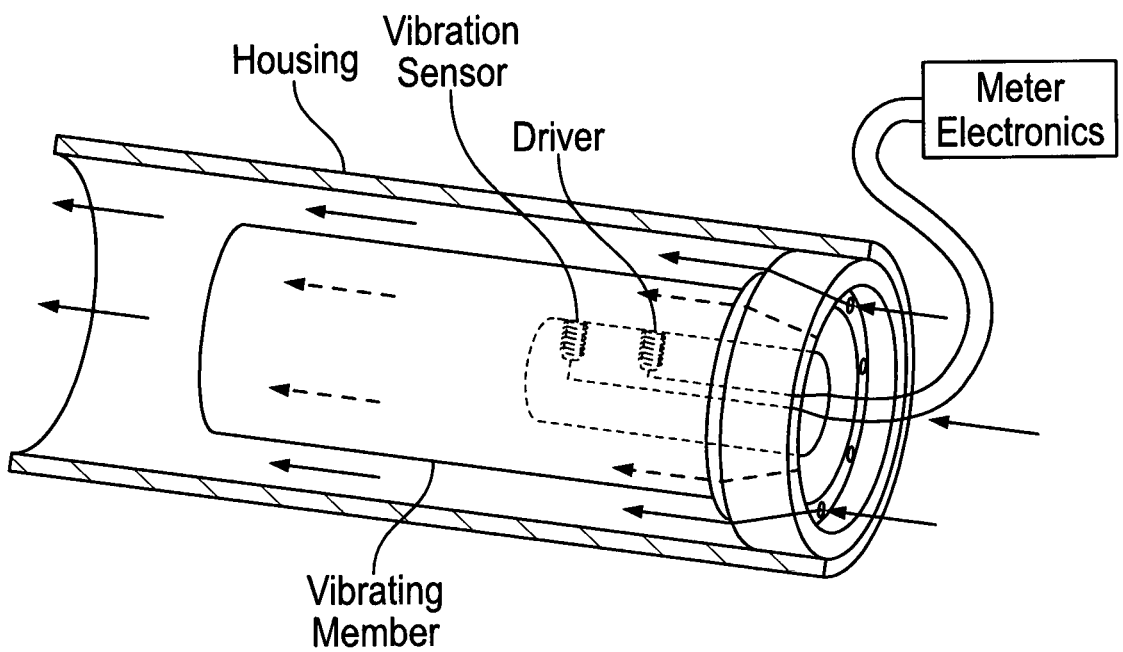
FIG. 4 shows a prior art densitometer.

The vibrating tube portion 104 comprises the element for density-sensing. The vibrating tube portion 104 may comprise a thin metal tube in some embodiments. In operation, the vibrating tube portion 104 is activated so that it vibrates in a radial mode at its natural frequency (see FIGS. 2 and 3, for example). The vibrating member 100 (and therefore the vibrating tube portion 104) is configured to be vibrated in one or more radial vibration modes. A fluid may be passed over the inner surface 110 and/or the outer surface 112 of the vibrating tube portion 104, and so fluid is therefore in contact with exposed sides of the vibrating tube portion 104. The mass of a fluid, which vibrates with the tube, depends upon the fluid density. Since increasing the vibrating mass decreases the natural frequency of vibration, the fluid density is determined by measuring the natural or resonant vibration frequency of the vibrating member 100 when the vibrating member 100 is vibrated in the presence of a fluid. The fluid is a gas, liquid, a liquid with suspended particulates and/or entrained gas, or combinations thereof.

Figure 7:
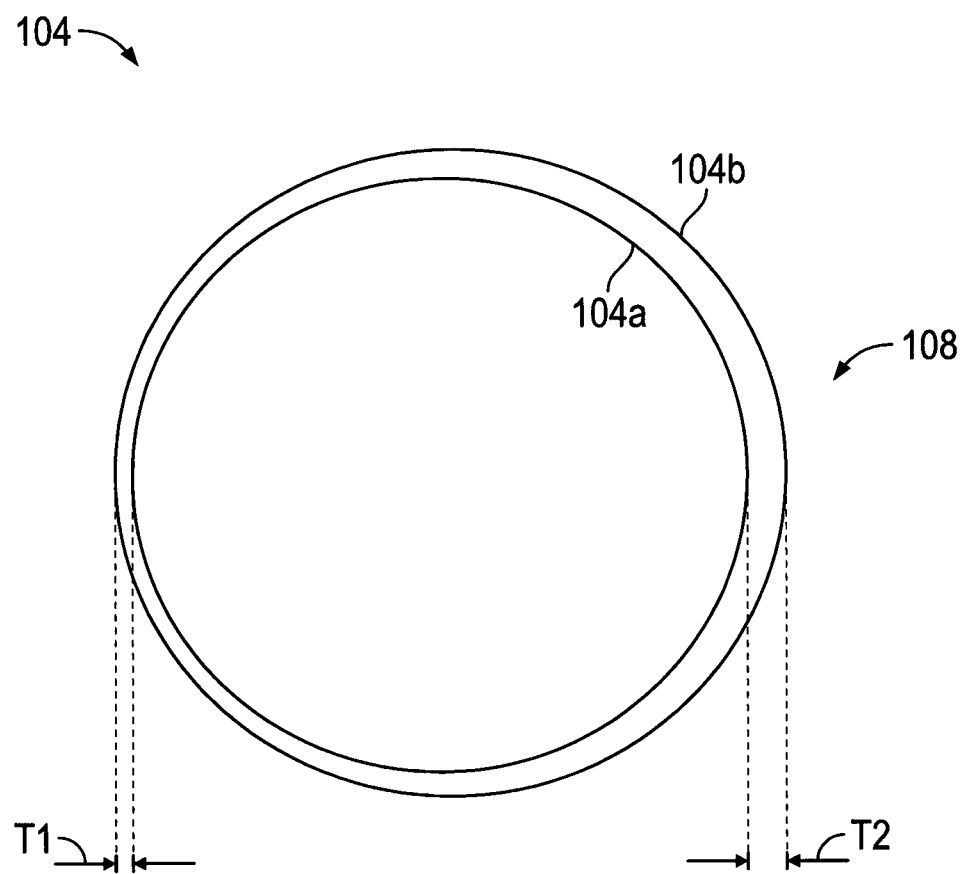
FIG. 7 shows a cross section of the vibrating member of FIG. 5.

With continuing reference to FIG. 5, and additionally turning to FIG. 7, in an embodiment, the vibrating tube portion 104 has an inner diameter 104a that is axially shifted from its outer diameter 104b. Therefore the inner diameter 104a is not concentric with the outer diameter 104b. This creates a cylinder with variable wall thickness, such that a first thickness, T1, is less than a second thickness, T2. In an embodiment, T1 and T2 are located in diametrically opposite sides of the vibrating tube portion 104. Though circular diameters are illustrated, an oblong cross-section is also contemplated. In an embodiment, T1 is the thinnest region along the vibrating tube portion's 104 circumference, while T2 is the thickest region of the vibrating tube portion's 104 circumference. Therefore, the wall thickness between T1 and T2 is continually variable, forming a gradient of wall thickness that increases from T1 to T2 along the circumference of the vibrating tube portion 104. It should be clear that the stiffness of the vibrating tube portion 104 corresponds to the thickness of the vibrating tube portion 104, so the stiffness increases from T1 to T2 along the circumference of the vibrating tube portion 104. It should also be understood that as the stiffness is changed along the circumference, a frequency separation correspondingly changes. It should also be noted that the smooth, continuous, surface of the vibrating tube portion 104 results in a relatively high Q factor, and is thus easily vibratable, yet still possesses the ability to separate frequencies. The frequency separation comprises a frequency separation between vibration modes, such as radial vibration modes. For example, the frequency separation can comprise a frequency separation between a first radial vibration mode and a second radial vibration mode. As a result, the frequency separation between the first vibration mode and the second vibration mode can be chosen by the designer of the vibrating densitometer 200 by the appropriate thickness selection of the vibrating tube portion 104 as well as the axial shift between the inner and outer diameters 104a, 104b.

In some embodiments, the vibrating tube portion 104 has an average wall thickness between about 0.08 mm and 0.25 mm. In an embodiment, the average wall thickness is about 0.12 mm. In an embodiment, the axial shift is between about 0.02 mm and 0.06 mm. In an embodiment, the axial shift is about 0.045 mm. In an embodiment, the first thickness, T1, is between about 0.02 mm and about 0.30 mm, and the second thickness, T2, is between about 0.02 mm and about 0.30 mm. In some embodiments, the distance of the axial shift can be selected to provide a desired frequency separation. According to an embodiment, the frequency separation between the intended drive mode and unintended modes will equal or exceed a threshold amount. For example, some embodiments may require that the lower frequency three-lobed radial vibration mode is separated from the next closest vibration mode by at least 10 Hz. It should be appreciated however, that 10 Hz is merely one example and the particular frequency separation will vary from one application to another and should in no way limit the claims that follow. In embodiments, the frequency separation is between about 2 Hz and about 200 Hz. In an embodiment, the frequency separation is between about 5 Hz and about 50 Hz. The current embodiments use the new and unique geometry of the axially shifted diameters of the vibrating tube portion 104 to separate the two frequencies, to improve design robustness, and to make the design less sensitive to manufacturing tolerances.

As a non-limiting illustrative example, a vibrating tube portion 104 having an average wall thickness of about 0.115 mm and an axial shift of about 0.045 mm would have a first thickness, T1, of about 0.07 mm and a second thickness, T2, of about 0.16 mm. These values are reflected at a point in FIG. 9, which is a graph illustrating the frequency separation between a first radial vibration mode and a second radial vibration mode. A vibrating tube portion 104 having a T2 thickness of 0.16 mm yields a frequency separation of about 47 Hz. It should be noted that in a perfectly round vibrating tube portion 104, the difference between these same modes would be nearly indistinguishable.

Figure 8:
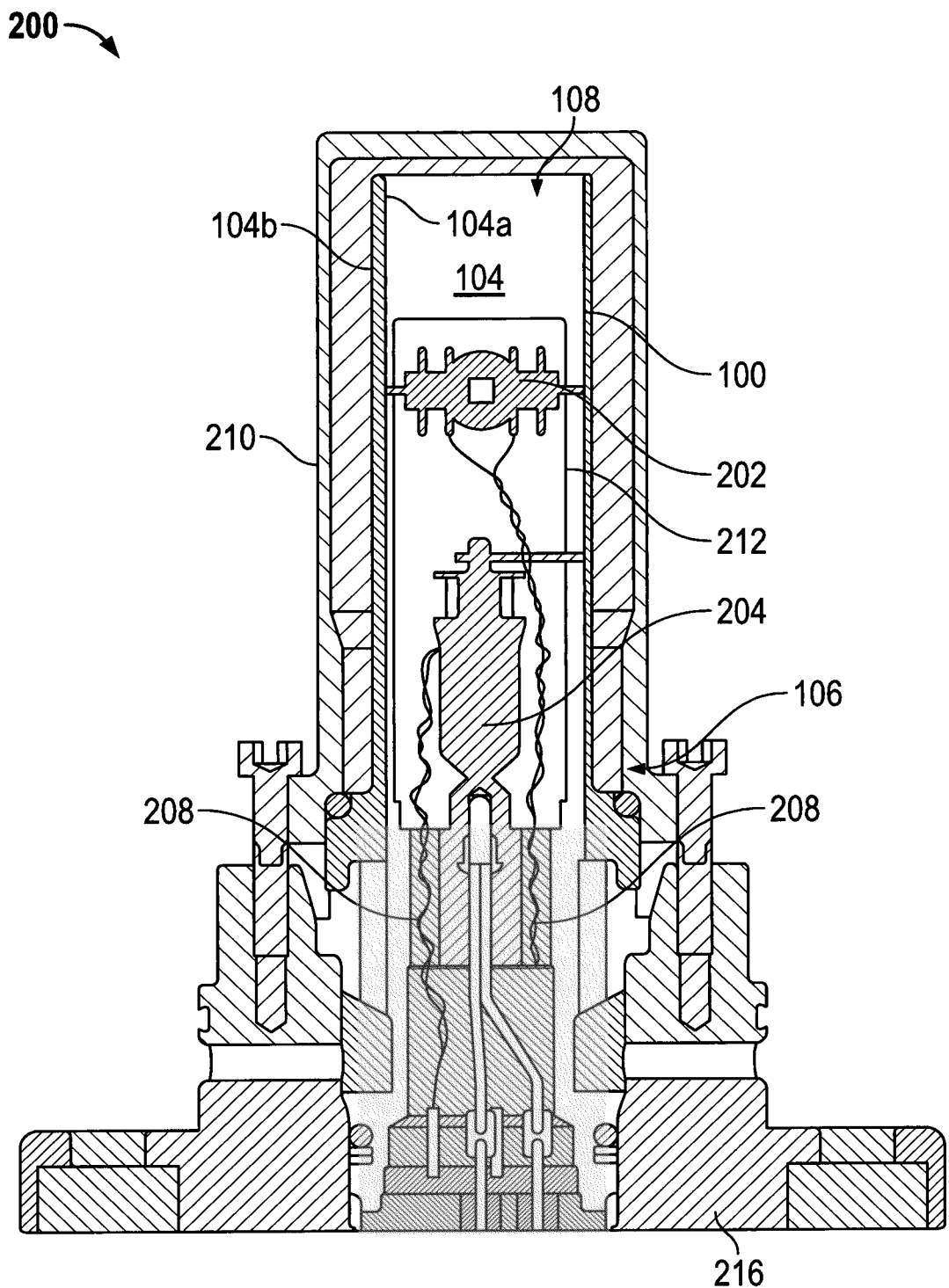
FIG. 8 shows a cross section of a vibrating densitometer according to an embodiment.
Figure 9:
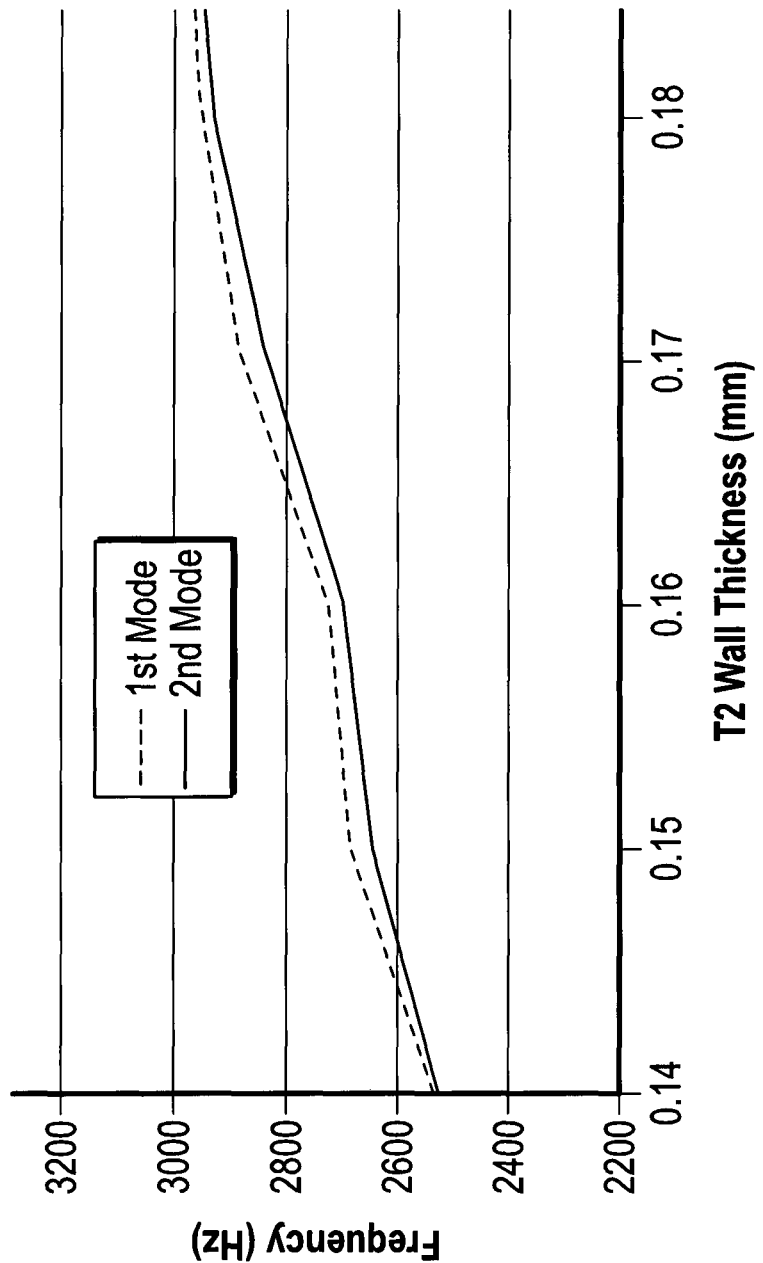
FIG. 9 is a graph of vibration frequency versus vibrating member wall thickness, illustrating the effect of wall thickness on frequency separation between first and second radial vibration modes in a vibrating densitometer.

Turning back to FIG. 6 and introducing FIG. 8, a vibrating densitometer 200 is illustrated according to an embodiment. The vibrating densitometer 200 may be configured to determine a density of a fluid, such as a gas, a liquid, a liquid with entrained gas, a liquid with suspended particulates and/or gas, or a combination thereof.

According to an embodiment, the vibrating densitometer 200 includes the vibrating member 100 inside a housing 210. The vibrating member 100 may be permanently or removably affixed to the housing 210. The fluid to be quantified may be introduced into or may be passed through the housing 210. The vibrating member 100 may be substantially coaxial within the housing 210 in some embodiments. However, the vibrating member 100 need not completely correspond to the housing 210 in cross-sectional shape.

When the vibrating tube portion 104 is installed in the vibrating densitometer 200, the inlet end 106 of the vibrating member 100 is coupled to the housing 210 while the outlet end 108 is free to vibrate. The vibrating tube portion 104 is not directly coupled to the housing 210 in the embodiment shown, but instead the base 102 is coupled to the housing 210 and the outlet end 108 is free to vibrate. As a result, the vibrating tube portion 104 is cantilever-mounted to the housing 210.

According to an embodiment, the vibrating densitometer 200 can further include a driver 202 and at least one vibration sensor 204, which can be coupled to a central tower 212. The driver 202 can be adapted to vibrate the vibrating member 100 in one or more vibration modes. While the driver 202 is shown located within a central tower 212 positioned within the vibrating member 100, in some embodiments the driver 202 may be positioned between the housing 210 and the vibrating member 100, for example. Furthermore, it should be appreciated that while the driver 202 is shown positioned closer to the inlet end 106, the driver 202 may be positioned at any desired location. According to an embodiment, the driver 202 can receive an electrical signal from the meter electronics 206 via leads 208. In the embodiment shown, the at least one vibration sensor 204 is coaxially aligned with the driver 202. In other embodiments, the at least one vibration sensor 204 may be coupled to the vibrating member 100 in other locations. For example, the at least one vibration sensor 204 may be located on an outer surface of the vibrating member 100. Further, the at least one vibration sensor 204 may be located outside the vibrating member 100 while the driver 202 is located inside the vibrating member 100, or vice versa.

The at least one vibration sensor 204 can transmit a signal to the meter electronics 206 via leads 208. The meter electronics 206 can process the signals received by the at least one vibration sensor 204 to determine a resonant frequency of the vibrating member 100. In an embodiment the driver 202 and vibration sensor 204 are magnetically coupled to the vibrating member 100, thus the driver 202 induces vibrations in the vibrating member 100 via a magnetic field, and the vibration sensor 204 detects vibrations of the vibrating member 100 via changes in a proximate magnetic field. If a fluid under test is present, the resonant frequency of the vibrating member 100 will change inversely proportionally to the fluid density as is known in the art. The proportional change may be determined during an initial calibration, for example. In the embodiment shown, the at least one vibration sensor 204 also comprises a coil. The driver 202 receives a current to induce a vibration in the vibrating member 100 and the at least one vibration sensor 204 uses the motion of the vibrating member 100 created by the driver 202 to induce a voltage. Coil drivers and sensors are well known in the art and a further discussion of their operation is omitted for brevity of the description. Furthermore, it should be appreciated that the driver 202 and the at least one vibration sensor 204 are not limited to coils, but rather may comprise a variety of other well-known vibrating components, such as piezo-electric sensors, laser sensors, etc., for example. Therefore, the present embodiment should in no way be limited to coils. Furthermore, those skilled in the art will readily recognize that the particular placement of the driver 202 and the at least one vibration sensor 204 can be altered while remaining within the scope of the present embodiments.

The meter electronics 206 may be coupled to a bus 214 or other communication link. The meter electronics 206 may communicate density measurements over the bus 214. The meter electronics 206 may also transmit any manner of other signals, measurements, or data over the bus 214. In addition, the meter electronics 206 may receive instructions, programming, other data, or commands via the bus 214.

In operation, the wall of the vibrating tube portion 104 is excited in a radial direction and in a radial vibration mode by a driver 202 or other excitation mechanism. The wall of the vibrating tube portion 104 will then vibrate in a corresponding radial mode, but at a resonant frequency of the elongated vibrating tube portion 104 and the surrounding flow fluid. The relationship between the driving force of the vibration and the asymmetry of the tube wall will cause one or more of the mode shapes to be excited.

The vibrating tube portion 104 separates the resulting vibration modes by at least a predetermined frequency difference, making discrimination between the vibration modes practical. Consequently, the vibrating densitometer 200 can filter or otherwise separate or discriminate the vibration modes picked up by the at least one vibration sensor 204. For example, the vibrating tube portion 104 can separate and space apart a lower frequency radial vibration mode from a higher frequency radial vibration mode. During construction of the vibrating member 100, the vibrating tube portion 104 and the base 102 are formed. In an embodiment, the vibrating member 100 is at least partially formed by machining. In an embodiment, the vibrating member 100 is at least partially formed by electrical discharge machining. These methods provide non-limiting examples of potential construction techniques, and do not serve to limit the use of other construction techniques. As will be clear to one skilled in the art, the vibrating tube portion 104 is formed, with the vibrating tube portion 104 comprising an inner diameter 104$a$ that is axially shifted from its outer diameter 104$b$. The inner diameter 104$a$ is formed to not be concentric with the outer diameter 104$b$, such that the vibrating tube portion 104 has variable wall thickness, such that a first thickness, T1, is less than a second thickness, T2. In an embodiment, T1 and T2 are located in diametrically opposite sides of the vibrating tube portion 104.

The vibrating tube portion 104 may be the same piece of material as the base 102. In an embodiment, the vibrating tube portion 104 is formed and subsequently affixed to the base 102. The vibrating tube portion 104 may be welded or brazed to the base 102 in some embodiments. However, it should be understood that the vibrating tube portion 104 may be affixed to the base 102 in any suitable manner, including being permanently or removably affixed to the base 102. Due to the shape of the vibrating tube portion 104, in an embodiment, the rotational orientation of the base 102 as mounted on a densitometer body 216 is not critical, thus assembly is simplified and portions of the vibrating densitometer 200 for rotationally orienting the vibrating member 100 may be omitted, thus simplifying assembly and reducing associated costs.

Although the discussion herein concerns a vibrating tube that is fixed at one end and free at the other end, it should be understood that the concepts and examples also apply to a tube that is fixed at both ends and is vibrated in a radial mode.

The detailed descriptions of the above embodiments are not exhaustive descriptions of all embodiments contemplated by the inventors to be within the scope of the present description. Indeed, persons skilled in the art will recognize that certain elements of the above-described embodiments may variously be combined or eliminated to create further embodiments, and such further embodiments fall within the scope and teachings of the present description. It will also be apparent to those of ordinary skill in the art that the above-described embodiments may be combined in whole or in part to create additional embodiments within the scope and teachings of the present description.

Thus, although specific embodiments are described herein for illustrative purposes, various equivalent modifications are possible within the scope of the present description, as those skilled in the relevant art will recognize. The teachings provided herein can be applied to other vibrating members, and not just to the embodiments described above and shown in the accompanying figures. Accordingly, the scope of the embodiments described above should be determined from the following claims.

What is claimed is:

1. A vibrating member (100) adapted for use in a vibrating densitometer (200) having a base (102) and a vibrating tube portion (104) affixed to the base (102), with the vibrating tube portion (104), comprising:
   an inner diameter (104a); and
   an outer diameter (104b), wherein the inner diameter (104a) is axially shifted from the outer diameter (104b) such that the inner diameter (104a) is not concentric with the outer diameter (104b), and wherein the axial shift increases a frequency separation between vibration modes in the vibrating tube portion (104).

2. The vibrating member (100) of claim 1, wherein the vibrating tube portion (104) is configured to be vibrated in one or more radial vibration modes.

3. The vibrating member (100) of claim 1, wherein the vibrating tube portion (104) comprises:
   a first cross-sectional portion having a first thickness (T1); and
   a second cross-sectional portion having a second thickness (T2), wherein the first thickness (T1) is smaller than the second thickness (T2).

4. The vibrating member (100) of claim 3, wherein the first thickness (T1) is diametrically opposed to the second thickness (T2).

5. The vibrating member (100) of claim 3, wherein a wall thickness of the vibrating tube portion (104) between the first thickness (T1) and the second thickness (T2) comprises a gradient of wall thickness that increases from the first thickness (T1) to the second thickness (T2) along a circumference of the vibrating tube portion (104).

6. The vibrating member (100) of claim 3, wherein the first thickness (T1) is between 0.02 mm and 0.30 mm, and the second thickness (T2) is between 0.02 mm and 0.30 mm.

7. The vibrating member (100) of claim 3, wherein the first thickness (T1) is between 0.04 mm and 0.09 mm, and the second thickness (T2) is between 0.14 mm and 0.18 mm.

8. The vibrating member (100) of claim 1, wherein the vibrating tube portion (104) comprises an average wall thickness between 0.08 mm and 0.25 mm.

9. The vibrating member (100) of claim 1, wherein the axial shift is between 0.02 mm and 0.06 mm.

10. The vibrating member (100) of claim 1, wherein the frequency separation between vibration modes in the vibrating tube portion (104) is between 2 Hz and 200 Hz.

11. The vibrating member (100) of claim 1, wherein the frequency separation between vibration modes in the vibrating tube portion (104) is between 5 Hz and 50 Hz.

12. The vibrating member (100) of claim 1, wherein the vibrating tube portion (104) is included in a housing (210) of a vibrating densitometer (200).

13. The vibrating member (100) of claim 12, wherein the vibrating densitometer (200) comprises:
   a driver (202) configured to vibrate the vibrating tube portion (104) with respect to the housing (210); and
   at least one vibration sensor (204) configured to detect vibrations of the vibrating tube portion (104).

14. A method of forming a vibrating member adapted for use in a vibrating densitometer, with the method comprising:
   forming a base;
   forming a vibrating tube portion comprising an inner diameter and an outer diameter, wherein the inner diameter is axially shifted from the outer diameter such that the inner diameter is not concentric with the outer diameter, and wherein the axial shift increases a frequency separation between vibration modes in the vibrating tube portion; and
   affixing the vibrating tube portion to the base.

15. The method of claim 14, comprising the step of configuring the vibrating tube portion to be vibrated in one or more radial vibration modes.

16. The method of claim 14, wherein the step of forming a vibrating tube portion comprises:
   forming a first cross-sectional portion having a first thickness; and
   forming a second cross-sectional portion having a second thickness, wherein the first thickness is smaller than the second thickness.

17. The method of claim 16, wherein the step of forming a vibrating tube portion comprises forming the first thickness to be diametrically opposed to the second thickness.

18. The method of claim 16, wherein the step of forming a vibrating tube portion comprises forming a wall thickness of the vibrating tube portion between the first thickness and the second thickness to be variable, thus forming a gradient of wall thickness that increases from the first thickness to the second thickness along a circumference of the vibrating tube portion.

19. The method of claim 16, wherein the step of forming a first cross-sectional portion comprises forming the first thickness to be between 0.02 mm and 0.30 mm, and forming the second thickness to be between 0.02 mm and 0.30 mm.

20. The method of claim 16, wherein the step of forming a first cross-sectional portion comprises forming the first thickness to be between about 0.04 mm and 0.09 mm, and forming the second thickness to be between 0.14 mm and 0.18 mm.

21. The method of claim 14, wherein the step of forming a vibrating tube portion comprises forming an average wall thickness of the vibrating tube portion to be between 0.08 mm and 0.25 mm.

22. The method of claim 14, wherein the axial shift is between 0.02 mm and 0.06 mm.

23. The method of claim 14, wherein the frequency separation between vibration modes in the vibrating tube portion is between 2 Hz and 200 Hz.

24. The method of claim 14, wherein the frequency separation between vibration modes in the vibrating tube portion is between 5 Hz and 50 Hz.

25. The method of claim 14, comprising the step of providing a housing of a vibrating densitometer configured to house the vibrating tube portion.

26. The method of claim 25, comprising the steps of: providing a driver configured to vibrate the vibrating tube portion with respect to the housing; and providing at least one vibration sensor configured to detect vibrations of the vibrating tube portion.

* * * * *

UNITED STATES PATENT AND TRADEMARK OFFICE
CERTIFICATE OF CORRECTION

PATENT NO. : 10,571,381 B2  
APPLICATION NO. : 15/559369  
DATED : February 25, 2020  
INVENTOR(S) : Felix Attila Farkas, Megan Casey and Roman Alexandru-Vlad Page 1 of 1

It is certified that error appears in the above-identified patent and that said Letters Patent is hereby corrected as shown below:

On the Title Page

Item [73], replace "Micron Motion, Inc." with --Micro Motion, Inc.--

In the Claims

Column 10, Line 53, Claim 20 replace "between about 0.04 mm" with --between 0.04 mm--

Signed and Sealed this  
Second Day of June, 2020

Andrei Iancu  
*Director of the United States Patent and Trademark Office*